United States Patent
El Matbouly et al.

(10) Patent No.: US 9,625,366 B2
(45) Date of Patent: Apr. 18, 2017

(54) MICROWAVE RESONATOR SENSOR AND ASSOCIATED METHODS OF SENSING

(71) Applicant: 3R Valo, société en commandite, Montreal (CA)

(72) Inventors: Hatem El Matbouly, Trois-Rivieres (CA); Frederic Domingue, Trois-Riviéres (CA)

(73) Assignee: 3R VALO, Société en commandite, Montréal (CA)

( * ) Notice: Subject to any disclaimer, the term of this patent is extended or adjusted under 35 U.S.C. 154(b) by 346 days.

(21) Appl. No.: 14/537,994

(22) Filed: Nov. 11, 2014

(65) Prior Publication Data

US 2015/0168314 A1    Jun. 18, 2015

Related U.S. Application Data

(60) Provisional application No. 61/902,552, filed on Nov. 11, 2013.

(51) Int. Cl.
*G01N 15/06* (2006.01)
*G01N 22/00* (2006.01)
(Continued)

(52) U.S. Cl.
CPC ............... *G01N 15/06* (2013.01); *G01K 7/32* (2013.01); *G01N 15/0606* (2013.01);
(Continued)

(58) Field of Classification Search
CPC ............... G01N 15/06; G01N 15/0606; G01N 15/0656; G01N 22/04; G01N 2015/0046;
(Continued)

(56) References Cited

U.S. PATENT DOCUMENTS 3,927,369 A    12/1975  Billeter et al.
4,604,898 A     8/1986  Gohin et al.
(Continued)

OTHER PUBLICATIONS

Elmatbouly et al., A Novel Chipless Identficaion Tag Based on a Substrate Integrated Cavity Resonator, Jan. 2013.
(Continued)

*Primary Examiner* — Hoai-An D Nguyen
(74) *Attorney, Agent, or Firm* — Norton Rose Fulbright Canada LLP; Alexandre Daoust (57) ABSTRACT

The sensor for sensing at least a physical property of an environment generally has a microwave resonator having a top conductive layer, a bottom conductive layer and a substrate layer therebetween, the substrate layer being made of a first dielectric material, a fence electrically connecting the top conductive layer to the bottom conductive layer across the substrate layer, and enclosing at least one resonance cavity, at least one microwave signal port across the fence, at least one sensing portion of a second dielectric material functionalized to the physical property of the environment, extending in the at least one resonance cavity and being exposed to the environment across at least one of the top conductive layer and the bottom conductive layer, the microwave resonator having at least one resonance frequency being dependent of the exposure of the second dielectric material with the environment to affect a microwave signal resonating therein.

26 Claims, 10 Drawing Sheets

(51) Int. Cl.
*G01N 33/00* (2006.01)
*G01K 7/32* (2006.01)
*G01N 22/04* (2006.01)
*G01N 15/00* (2006.01)

(52) U.S. Cl.
CPC ......... *G01N 15/0656* (2013.01); *G01N 22/04* (2013.01); *G01N 33/0036* (2013.01); *G01N 2015/0046* (2013.01)

(58) Field of Classification Search
CPC ............... G01N 33/0036; G01N 17/00; G01N 21/7746; G01N 2021/7789; G01N 27/122; G01N 29/42; G01R 23/07; G01R 23/08; G01R 27/00; G01R 27/26; G01R 27/2605; G01D 5/24; G01D 5/2405; G01K 7/32; G06K 19/0726
USPC ....... 324/600, 629, 633, 649, 652, 658, 663, 324/674, 675, 681, 682, 691, 707, 708, 324/76.11, 76.39, 76.51
See application file for complete search history.

(56) References Cited

U.S. PATENT DOCUMENTS

| | | | | |
|---|---|---|---|---|
| 4,633,180 | A * | 12/1986 | Biehl | G01R 33/343 324/316 |
| 5,489,988 | A | 2/1996 | Ackley et al. | |
| 5,585,722 | A * | 12/1996 | Hosoki | B82Y 35/00 324/300 |
| 5,774,603 | A | 6/1998 | Moore et al. | |
| 6,031,944 | A | 2/2000 | Youngner | |
| 7,059,192 | B2 | 6/2006 | Correale et al. | |
| 7,104,182 | B2 | 9/2006 | Reininger | |
| 7,151,380 | B2 | 12/2006 | Typpo et al. | |
| 7,368,311 | B2 | 5/2008 | Tilmans et al. | |
| 7,756,667 | B2 * | 7/2010 | Hamann | G01K 1/026 374/141 |
| 2004/0086020 | A1 * | 5/2004 | Jordahl | G01K 3/005 374/45 |
| 2005/0109095 | A1 | 5/2005 | Sinnett | |
| 2007/0146718 | A1 | 6/2007 | Takase et al. | |
| 2008/0146890 | A1 | 6/2008 | Leboeuf et al. | |
| 2011/0018657 | A1 | 1/2011 | Cheng et al. | |
| 2012/0068690 | A1 | 3/2012 | Song et al. | |
| 2012/0248887 | A1 | 10/2012 | Kesler et al. | |
| 2013/0081447 | A1 | 4/2013 | Carter et al. | |
| 2013/0119135 | A1 | 5/2013 | Gauthier et al. | |

OTHER PUBLICATIONS

Deslandes, Integrated Microstrip and Rectangular Waveguide in Planar Form, vol. II, No. 2 Feb. 2001.
Cassivi, Low Cost Microwave Oscillator Using Substrate Integrated Waveguide Cavity, vol. 13, No. 2 Feb. 2003.
Moro, Novel Inkjet-Printed Substrate Integrated Waveguide (SIW) Structures on Low-Cost Materials for Wearable Applications, Oct. 29-Nov. 1, 2012.
Hong, Simulation and Experiment on SIW Slot Array Antennas, vol. 14, No. 9, Sep. 2004.
Deslandes, Single-Substrate Integration Technique of Planar Circuits and Waveguide Filters, vol. 51. No. 2, Feb. 2003.
Fraden, Handbook of Modern Sensors, Chapter 11 "Flow Sensors" 2010.
Wu, The Substrate Integrated Circuits—A New Concept for High-Frequency Electronics and Optoelectronics, Dec. 2003.
MNT Gas Sensor Forum, MNT Gas Sensor Roadmap, Dec. 2006, Dec. 14, 2006.

* cited by examiner

MICROWAVE RESONATOR SENSOR AND ASSOCIATED METHODS OF SENSING

CROSS-REFERENCE TO RELATED APPLICATIONS

This patent application claims priority of U.S. provisional Application Ser. No. 61/902,552, filed on Nov. 11, 2013, the contents of which are hereby incorporated by reference herein.

BACKGROUND OF THE INVENTION

Field of the Invention

The improvements generally relate to the field of sensors for sensing physical properties of an environment, and more particularly to a sensor using a microwave resonator.

The improvements generally relate to the field of sensors for sensing physical properties of an environment, and more particularly to a sensor using a microwave resonator.

Sensors for sensing physical properties of an environment are well known in the art. Recently, sensors for monitoring air quality such as gas presence, humidity level, a temperature or dust level in vehicles, houses, and offices have raised a high degree of interest in science.

Although existing sensors were satisfactory to a certain degree, there remained room for improvement, particularly in terms of providing passive sensors adapted to the physical property to sense, of providing sensors that can be individually identifiable by a signature tag, and of providing sensors that can be remotely interrogated and that allow these sensors to be manufactured at a competitive cost.

SUMMARY OF THE INVENTION

In accordance with one aspect, there is provided a substrate-integrated waveguide (SIW) sensor reactive to a microwave signal and enabling to sense environmental physical properties such as a presence of a gas, a humidity level, a temperature, a dust level, etc.

In accordance with another aspect, there is provided a sensor having a microwave resonator in which an input microwave signal can be propagated, resonated to allow interaction with the environment, and a characteristic representative of the interaction with the environment can be measured in the output microwave signal. The microwave resonator can be characterized, for instance, by a given effective permittivity value and by a given shape. Henceforth, for the given effective permittivity value and the given shape, the microwave resonator can have a signature resonance frequency. It is known in the art that upon a physical property change around a dielectric material, the effective permittivity of the dielectric material can change accordingly. Therefore, the sensor is adapted to sense a change of the physical property through a change in the effective permittivity value of its microwave resonator.

In other words, a microwave signal having a broad spectrum that is propagated through the microwave resonator can be transformed into a microwave output signal having a resonance frequency dip in its frequency spectrum. The resonance frequency dip can be attributed to the frequencies resonating (trapped) in the microwave resonator. Now, since the resonance frequency can depend on the effective permittivity value of the microwave resonator, any change in the environment of the microwave resonator can be sensed by a shift of the resonance frequency dip of the output microwave signal. It is readily understood that higher order resonance frequencies can also resonate within the resonator. Consequently, the shift of the resonance frequency can be measured on a first order of resonance (first mode), as it can be measured on a second order of resonance (second mode), or on a third order of resonance (third mode), and so on. As it may be understood by one skilled in the art, the shift of resonance frequency of the second order or resonance can be greater than the shift of resonance frequency of the first order for a given physical property variation, thus offering a greater sensitivity.

In accordance with another aspect, there is provided a sensor having a microwave resonator characterized by an enhanced sensitivity due to the high quality factor of its resonator (or resonant cavity). It is known in the art that quality factors can be a convenient measure for a sensor's sensitivity. Indeed, the quality factor of a resonator is as high as the width of its resonance frequency is narrow. Practically, a narrower resonance frequency can enable the measurement of a smaller increment of the physical property.

In accordance with another aspect, there is provided a sensor that has a microwave resonator having a top conductive layer, a bottom conductive layer and a dielectric substrate layer therebetween. More particularly, the top conductive layer and the substrate layer has at least one sensing portion integrated therethrough to form at least one resonance cavity, the at least one sensing portion being functionalized with a sensitive dielectric material adapted to the physical property to sense. Differently put, there is provided a sensor having a microwave resonator that can be characterized by a given effective permittivity value, the latter being determined, for instance, at least by the dielectric constant of the substrate layer and by the sensitive dielectric constant of the dielectric material filing the at least one sensing portion. Therefore, if the sensitive dielectric material is known to vary in an enhanced manner according to a given physical property, the sensor can be more sensitive to this given physical property. For instance, the sensitive dielectric material can be air for humidity sensing, and can be tin dioxide for sensing the presence of hydrogen.

In accordance with another aspect, there is provided a sensor only having passive components therein.

In accordance with another aspect, there is provided a sensor that can be passively interrogated using electrical wires to be connected to a microwave signal port, or wirelessly interrogated using a microwave antenna connected to the microwave resonator of the sensor.

In accordance with another aspect, there is provided a sensor that has a microwave resonator having a given pattern of sensing portions disposed therethrough. Since a resonance frequency of the microwave resonator can be dependent on a given shape of the microwave resonator for instance, the microwave resonator of the sensor having the given pattern of sensing portions can have a signature resonance frequency. Therefore, a first sensor having a first pattern of sensing portions disposed through the microwave resonator can be distinguished from a second sensor having a second pattern of sensing portions disposed therethrough. Accordingly, by measuring the resonance frequency of a particular sensor, one can determine which sensor it is and consequently, determine which physical property is being sensed. Moreover, the sensor can be integrated with other systems by using radio frequency components hence increasing their compatibility and functionality.

In accordance with another aspect, there is provided a sensor for sensing at least a physical property of an environment, the sensor comprising a microwave resonator having a top conductive layer, a bottom conductive layer and a substrate layer therebetween, the substrate layer being made of a first dielectric material, a fence electrically connecting the top conductive layer to the bottom conductive layer across the substrate layer, and enclosing at least one resonance cavity, at least one microwave signal port across the fence, at least one sensing portion of a second dielectric material functionalized to the physical property of the environment, extending in the at least one resonance cavity and being exposed to the environment by at least one of the top conductive layer and the bottom conductive layer, the microwave resonator having at least one resonance frequency being dependent of the exposure of the second dielectric material with the environment to affect a microwave signal resonating therein.

In accordance with another aspect, there is provided a method for sensing at least a physical property of an environment, the method comprising: providing a path having an input and an output; and a microwave resonator therebetween, the microwave resonator having a top conductive layer, a bottom conductive layer and a substrate layer therebetween, the top conductive layer being electrically connected to the bottom conductive layer by a conductive fence across the substrate layer, the fence enclosing at least one resonance cavity, the input being connected to the at least one resonance cavity across the fence, each of the at least one resonance cavity having at least one sensing portion of a second dielectric material functionalized to the physical property of the environment, extending in the at least one resonance cavity and being exposed to the environment across at least one of the top conductive layer and the bottom conductive layer, the microwave resonator having at least one resonance frequency; propagating an input microwave signal into the input of the path, the microwave resonator transforming the input microwave signal into an output microwave signal being characterized by the at least one resonance frequency, the at least one resonance frequency being dependent of the exposure of the second dielectric material with the environment to affect a microwave signal resonating therein; measuring the resonance frequency in the output microwave signal from the output of the path; and sensing the at least a physical property based on the resonance frequency.

In accordance with another aspect, there is provided a method of making a sensor for sensing at least a physical property of an environment, the method comprising: placing a substrate layer made of a first dielectric material; incorporating a layer of conductive material on the top of the substrate and a layer of conductive material on the bottom of the substrate; processing at least one sensing portion through the three layers thus forming a fence of through-holes enclosing at least one resonance cavity of the three layers; processing an input channel on the layer of conductive material on the top of the substrate, the input channel protruding to one of the at least one resonance cavity of the three layers; processing, on the at least one resonance cavity, a given configuration of holes through at least the layer of conductive material on the top of the substrate and the substrate layer; applying a melted layer of conductive material on an interior surface of the through-holes thereby making an electrical link between the two layers of conductive material; and inserting a dielectric material inside the holes of at least an associated resonance cavity.

Many further features and combinations thereof concerning the present improvements will appear to those skilled in the art following a reading of the instant disclosure.

BRIEF DESCRIPTION OF THE DRAWINGS

For a fuller understanding of the nature and objects of the invention, reference should be had to the following detailed description taken in connection with the accompanying drawings in which:

FIG. 2A is a block diagram showing an example of a substrate-integrated waveguide sensor having an antenna for remote interrogation or wireless communication with an electrical spectrum analyser while

FIG. 4A is a graph showing an example of the relative variation of the relative permittivity of tin dioxide as a function of frequency with and without presence of hydrogen while

FIG. 6A is an oblique view of an alternate example of a substrate-integrated waveguide sensor having three resonance cavities on the top conductive layer of the sensor while

DETAILED DESCRIPTION OF THE PREFERRED EMBODIMENT

Figure 1:
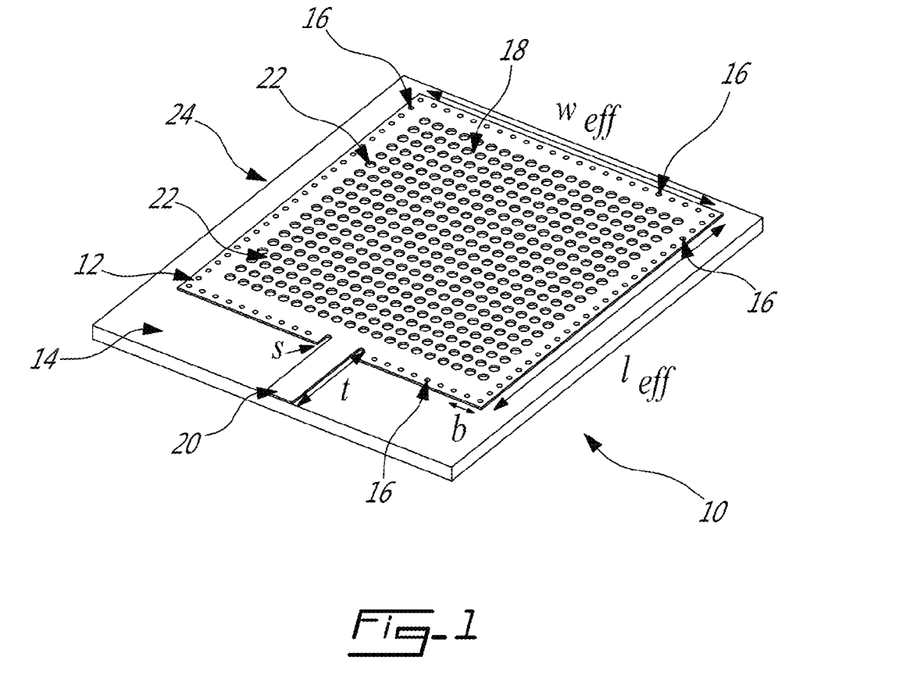
FIG. 1 is an oblique view of an example of a microwave resonator of a substrate-integrated waveguide sensor.

FIG. 1 shows an example of a substrate-integrated waveguide (SIW) sensor 10. The sensor 10 can have a microwave resonator that has a top conductive layer 12, a bottom conductive layer and a substrate layer 14 therebetween. The substrate layer 14 is generally made of a dielectric material while the top conductive layer 12 and the bottom conductive later can be made of a metallic material such as copper, for instance. The top conductive layer 12 can be electrically connected to the bottom conductive layer with a fence, or a fence of via holes 16 enclosing one or many resonance cavities 18. Via holes are known in the electronic arts and are generally used to electrically connect different layers of a substrate. They typically consist of holes having their inside surface covered with a conductive material, for instance. On the other hand, it is understood that any type of fence can be used in order to electrically connect the top conductive surface 12 and the bottom conductive surface. It is important, for any design of fence, that the microwave signal can be reflected from the fence in order to resonate within the resonant cavity.

Additionally, the microwave resonator can have a microwave signal port 20 across the fence 16 and connecting the top conductive layer 12 for receiving a signal to be propagated to the resonant cavities. Particularly, each of the resonance cavities 18 can have a signature pattern of sensing portions 22 through at least the top conductive layer and the substrate layer thereunder (or through the bottom conductive surface in another embodiment). Each sensing portion can be provided in the form of a hole through either the top conductive layer and the substrate layer, or the top conductive layer, the substrate layer and the bottom conductive layer. To facilitate the manufacturing process, each sensing portion can be drilled through the microwave resonator, for instance. To obtain the sensing portions 22, the sensing portions of the resonance cavity can be filled with an associated dielectric material which is assumed particularly sensitive to a physical property to sense. It is understood that each of the resonance cavities 18 imparts an associated resonance frequency to the microwave resonator, and that the resonance frequency varies as a function of the physical property of an environment therearound.

It is understood that the sensor can have a body having any two-dimensional shape such as a circular body, a triangular body, or other polygonal bodies. Referring to FIG. 1, however, the sensor 10 can have a rectangular body 24. The dimensions of the rectangular body 24 can have an impact on the resonance frequency of the microwave resonator of the sensor 10. Henceforth, it is possible to compute the resonance frequency of the rectangular microwave resonator using the equation:

$$f_r = \frac{c}{2\sqrt{\varepsilon_r}} \sqrt{\left(\frac{n}{w_{\mathit{eff}}}\right)^2 + \left(\frac{m}{l_{\mathit{eff}}}\right)^2}, \quad (1)$$

where $f_r$ is the resonance frequency of the microwave resonator, c relates to the speed of an electromagnetic wave in vacuum, $\varepsilon_r$ is the relative permittivity of the substrate layer 14, n and m indicates integers representative of the mode of the resonator, weff and leff are the effective width and length of the microwave resonator which are determined by the fence of via holes 16 enclosing the resonance cavity 18 and the microwave signal port 20. The effective dimensions are determined by the equations:

$$w_{\mathit{eff}} = w_i - \frac{D}{0.95b} \text{ and } l_{\mathit{eff}} = l_i - \frac{D}{0.95b} \quad (2)$$

where the indices eff indicates the effective dimensions, the indice i indicates the distance between two opposite sides of the fence of via holes, D is the diameter of the via holes of the fence of via holes 16 and b is a via hole spacing.

The microwave signal port 20 adjoining a subminiature version A (SMA) connector to the microwave resonator can be provided in the form of a microstrip transmission line adapted to the microwave resonator. Indeed, the microwave signal port 20 can propagate the microwave input signal to the microwave resonator, where the input microwave signal is transformed into an output microwave signal which can be later propagated back to the SMA connector via the microwave signal port 20.

The given pattern of sensing portions 22 introduced above can be holes to be filled with ambient air, i.e. a dielectric known to change its permittivity as a function of the humidity level of the environment, or it can be filled with any dielectric material that are suited for sensing a change of a physical property of the environment. It is worthy to note that the number of sensing portions inside the microwave resonator can vary depending on the dielectric constant of the sensitive dielectric material filled therein. Experiments and materials known to be particularly sensitive to the presence of a gas, or other physical property, are presented further below. In one embodiment, the sensing portions 22 can go through both the top conductive layer 12 and the substrate layer 14, while the bottom conductive layer remains plain and can be used as a circuit ground. It is readily understood that the distance s (see FIG. 1), i.e. the distance between the microwave signal port 20 and the fence of via holes 16, can help in achieving a better coupling of the input microwave signal.

Figure 2A:
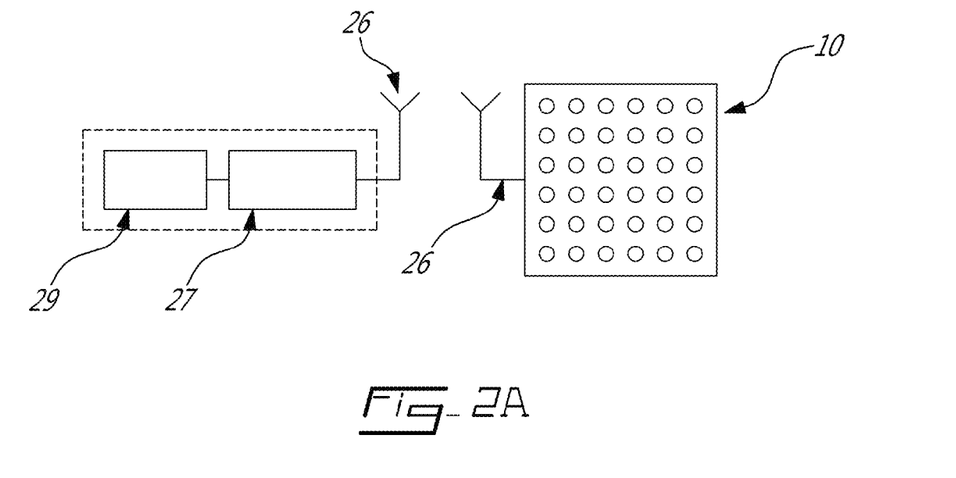

FIG. 2A shows an example of a bloc diagram showing the sensor 10 having an antenna 26 connected to the microwave resonator, the antenna 26 enabling remote interrogation of the sensor 10 or wireless communication with, for instance, an analyser 27 having a display 29. In this detection system, a broad microwave signal can be propagated to be received by the antenna 26 of the sensor 10. When the microwave signal is propagated through the microwave resonator of the sensor 10, a portion of the microwave signal can resonate in the resonator. Henceforth, the ESA can detect a reflected broad microwave signal having a dip representative of the portion of the microwave signal still resonating (to be subsequently attenuated) in the microwave resonator. Thus, sensing can be achieved by monitoring a spectral position of the frequency dip as a function of a physical property.

Figure 2B:
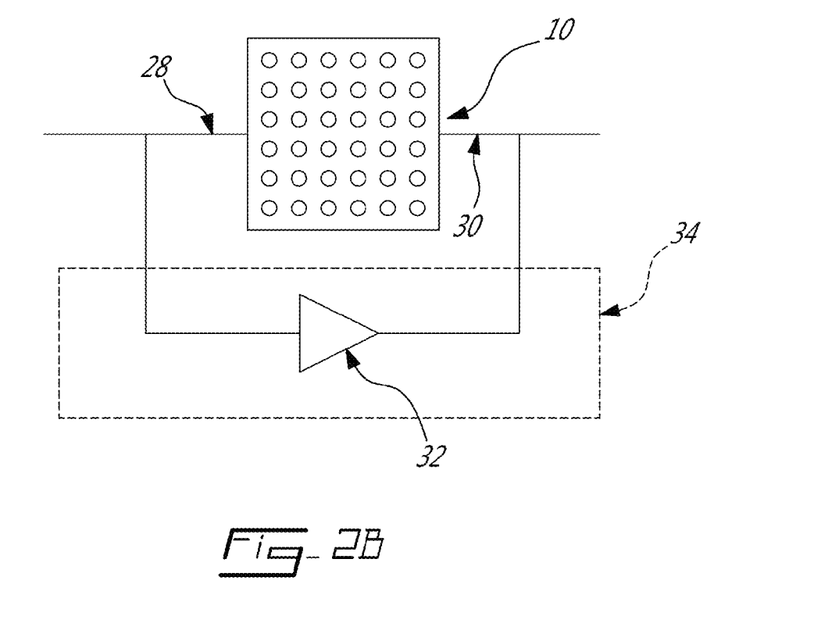
FIG. 2B is a block diagram showing an example of a substrate-integrated waveguide sensor used in a wired interrogation system.

FIG. 2B shows an alternate example of a detection system. In this embodiment, the sensor 10 has an input end 28 and an output end 30, where an input microwave signal can be provided to the input end 28, then transformed into an output microwave signal that can be measured with the output end 30. In another embodiment, the sensor 10 can have an amplifier 32 (or radio-frequency amplifier, RF amplifier) to form an amplification stage 34 (or loop of amplification).

Figure 3A:
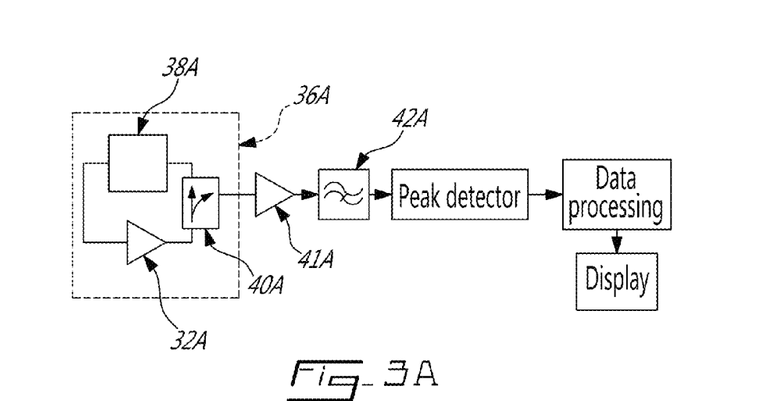
FIG. 3A is a block diagram showing an example of a detection system involving a sensing oscillator.
Figure 3B:
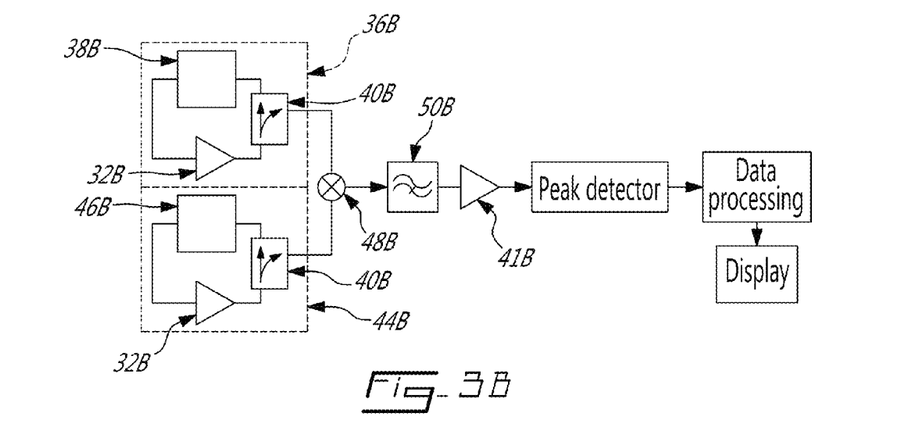
FIG. 3B is a block diagram showing an example of a detection system involving a sensing oscillator and a reference oscillator.
Figure 3C:
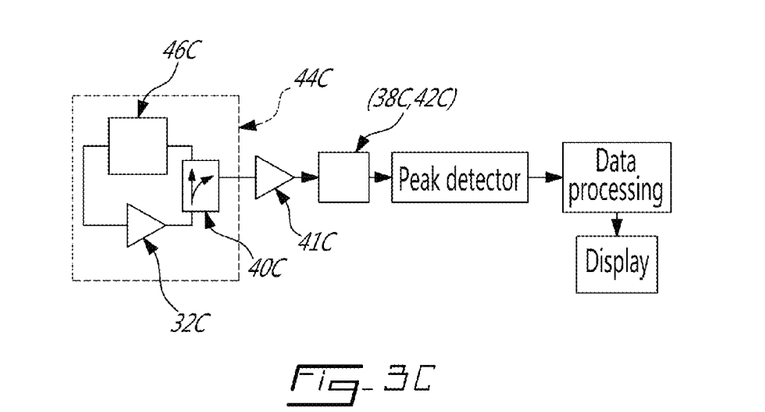
FIG. 3C is a block diagram showing an example of a detection system involving a reference oscillator connected to a high pass filter made using a functionalized substrate-integrated waveguide sensor.

FIGS. 3A-C show examples of detection systems which can be used to sense a physical property of an environment using one or more SIW sensors. FIG. 3A shows a detection system including a sensing oscillator 36A in which an active component such as a microwave amplifier 32A can be used as a seed to provide a base microwave signal. Since the microwave amplifier 32A of the sensing oscillator 36A is connected to a functionalized sensor 38A (sensor having a second dielectric material filing the sensing portions therein), microwave frequencies can be oscillated in the sensing oscillator 36A. A microwave power splitter 40A is used to propagate a portion of the microwave signal oscillating in the sensing oscillator 36A out of the oscillator to form an output signal. The output signal is then amplified using an output amplifier 41A and filtered using a high pass filter 42A. The output signal can later be analysed using a peak detector, a data processing computer and a display.

FIG. 3B shows an example of a detection system including a sensing oscillator 36B, and a reference oscillator 44B. The sensing oscillator has a functionalized sensor 38B, a microwave amplifier 32B, a microwave power splitter 40B, while the reference oscillator 44B has an unfunctionalized sensor 46B (or a sensor only functionalized with air), a microwave amplifier 32B, and a microwave power splitter 40B. Output signals of both the sensing oscillator 36B and of the reference oscillator 44B are then mixed using a mixer 48B. When the two output signals have a different frequency spectrum, a frequency beat can be generated. This beat generally has higher frequency components and lower frequency components (difference of the frequencies of the two oscillators), the higher frequency components can be filtered using a low pass filter 50B. Afterwards, the lower frequency components can be amplified using a microwave output amplifier 41B, hence allowing the resulting signal to be analysed using a peak detector, a data processing computer and a display.

FIG. 3C shows an example of a detection system including a reference oscillator 44C having an unfunctionalized sensor 44C, a microwave amplifier 32C, a microwave power splitter 40C. In this detection system, a microwave signal can be amplified in the reference oscillator 44C. The microwave signal directed out of the reference oscillator 44C by the microwave power splitter 40C can be amplified using a microwave output amplifier 41C, which can then be filtered using a band pass filter 42C made using a functionalized sensor 38C. The resulting signal being subsequently analysed using a peak detector, a data processing computer and a display. A characteristic of the band pass filter 42C, such as a cut off frequency, can change due to a change of the physical property, which affects the amplitude of the output signal thus indicating the change of physical property.

These detection systems allow easy integration of the above-mentioned microwave components directly on the PCB in which the substrate-integrated waveguide sensor is integrated, henceforth providing a monitoring circuit that does not require additional packaging and assembly. It can be noted that the SIW sensors can be manufactured in many other common planar technologies such as low temperature co-fired ceramic (LTCC), thick film, thick paper printing, and the like.

The substrate-integrated waveguide sensor is designed using an electromagnetic simulation software which allows to shape the three-dimensional structure of the microwave resonator and to perform a full-wave three-dimensional analysis. Based on given parameters, the software can estimate a signature resonance frequency, a phase thereof, and a distribution of the electric field inside the substrate-integrated microwave resonator. The effect of sensing portions inside the microwave resonator has been investigated with the software. For instance, perfect conductive material are assumed for the top conductive layer, the bottom conductive layer and the conductive material electrically connecting the top conductive layer to the bottom conductive layer in the via holes of the fence. In addition, absorbing boundary conditions were applied along the edges of the rectangular body (boundary walls of the body of the microwave resonator). For the simulation, the substrate chosen was the Roger substrate RO3004C having parameters such as an electric permittivity of $\in_r=3.55$, $\tan \delta=0.002$, a thickness of 1.524 mm and a copper thickness of 17 μm. The dimensions of the microwave resonator can be 31 mm×31 mm, which fixes the signature resonance frequency around 3.56 GHz for a resonance of first order (fundamental frequency mode TE10). This embodiment is shown in FIG. 1, and the parameters s, t, b, weff and leff are listed in Table 1. It is readily understood by one skilled in the art that the shape and the dimensions of the substrate-integrated waveguide sensor and microwave resonator thereof can be modified to obtain resonance frequencies other than frequencies around 3.56 GHz. The dimensions shown in Table 1 are exemplary only. Indeed, dimensions facilitating the manufacturing process (using PBC techniques) can be suitable for the sensor presented herein. For instance, common diameter for via holes can range from 0.3 mm to 1.0 mm.

TABLE 1

Values for parameters used to simulate the microwave cavity using the software:

| Parameter | weff [mm] | leff [mm] | s [mm] | t [mm] | via hole diameter [mm] | sensing portion diameter [mm] | b [mm] |
|---|---|---|---|---|---|---|---|
| Value* | 31 | 31 | 0.37 | 9.7 | 0.4 | 0.8 | 1.5 |

*Values given to the PCB prototyping machine used. The machine has a resolution of 0.5 μm and a repeatability of 0.001 mm. However, the resolution and the repeatability can vary from one prototyping machine to another.

As mentioned above, the substrate-integrated waveguide sensor described herein can have sensing portions in order to be particularly sensitive to a physical property to detect. Accordingly, Tables 2 and 3 list, respectively, sensitive dielectric materials associated to a gas to be detected and sensitive dielectric materials associated to humidity and temperature sensing. Also, it has to be noted that functionalized polymers can be used to facilitate the integration of sensitive materials in the microwave resonator using industrial PCB fabrication processes.

TABLE 2

Examples of sensitive dielectric material that can be used for sensing the presence of a given gas

| Gas to be detected | Sensitive dielectric material therefore |
|---|---|
| CO, $H_2$, $CH_4$ | $SnO_2$ (tin dioxide) |
| $NO_x$, $O_3$, $H_2S$, $SO_2$ | $WO_3$ |
| $O_2$, CO | $Ga_2O_3$ |
| $O_3$, $NO_x$ | $In_2O_3$ |
| $NH_3$, $NO_2$ | $MoO_3$ |
| $O_2$, CO, $SO_2$ | $TiO_2$ |
| $CH_4$, $C_4H_{10}$, $O_3$, $NO_x$ | ZnO |
| $H_2S$, $NH_3$, CO, volatile organic compounds | CrTiOx |
| Alcohol, $CH_4$, $NO_2$ | $Fe_2O_3$ |
| Formaldehyde | Perovskite oxide structure: $La_{1-x}Sr_xFeO_3$ (x = 0, 0.2, 0.5); Conductive polymer PPy/EBSA |
| $CO_2$ | Type electrolytic solid: $Na_{1+x}Zr_2Si_xP_{3-x}O_{12}$ (1.8 < x < 2.4); $Na_2CO_3$—$BaCO_3$, $Na_2CO_3$—$CaCO_3$, $Li_2CO_3$—$BaCO_3$, et $Li_2CO_3$—$CaCO_3$. |
| $NO_x$ | $WO_3$, ZnO, $SnO_2$, $In_2O_3$, $TiO_2$ |
| CO | $WO_3$, $In_2O_3$, $MoO_3$, $V_2O_5$ |
| $NH_3$ | nanofibres $WO_3$ polypyrrole (PPy)/$ZnSnO_3$ |
| $H_2S$ | $SnO_2$ doped by Ag ZnO nano-wires |

TABLE 3

Examples of sensitive dielectric material that can be used for sensing a given physical property

| Example of other physical property to be sensed | Sensitive dielectric material therefore |
|---|---|
| Humidity | Kapton 500HN polymer |
| Temperature | Epoxy/BaTiO$_3$ Composite |

Figure 4A:
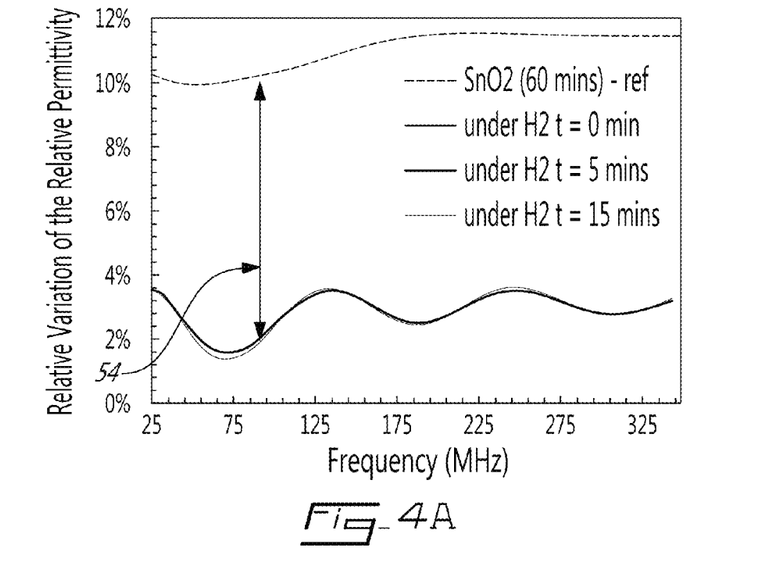

As listed in Table 2, tin dioxide can be used as a sensitive dielectric material to sense a presence of hydrogen in an environment. To integrate the tin dioxide into sensing portions of a given pattern of sensing portions, a tin dioxide powder having a grain size in the range of the nanometer can be used. Moreover, the grain size of the nano powder can be optimized in order to enhance the sensitivity of the material. FIG. 4A shows the relative variation of the relative permittivity of a nano powder of tin dioxide that has been grinded for 60 minutes when under a controlled environment in which hydrogen has been introduced. It is seen that the relative permittivity of the tin dioxide changes (see arrow 54) in the presence of hydrogen, which makes the tin dioxide a suitable dielectric material for sensing a presence of hydrogen in an environment. It was shown that among a nano powder that have not been grinded, a nano powder that have been grinded for 15 minutes, a nano powder that have been grinded for 30 minutes, a nano powder that have been grinded for 45 minutes and a nano powder that have been grinded for 60 minutes, the latter was the one exhibiting the largest relative variation of the relative permittivity in a given frequency range. As mentioned above, the tin dioxide tested can be provided in a matrix of polymer, for instance, to form a composite matrix. The composite matrix facilitates the incorporation of the nano powder in the sensing portions (holes) of the resonance cavity of the substrate-integrated waveguide sensor. It is understood that other polymer matrices can be used to form a composite matrix for the dielectric material proposed in Tables 2 and 3.

Figure 4B:
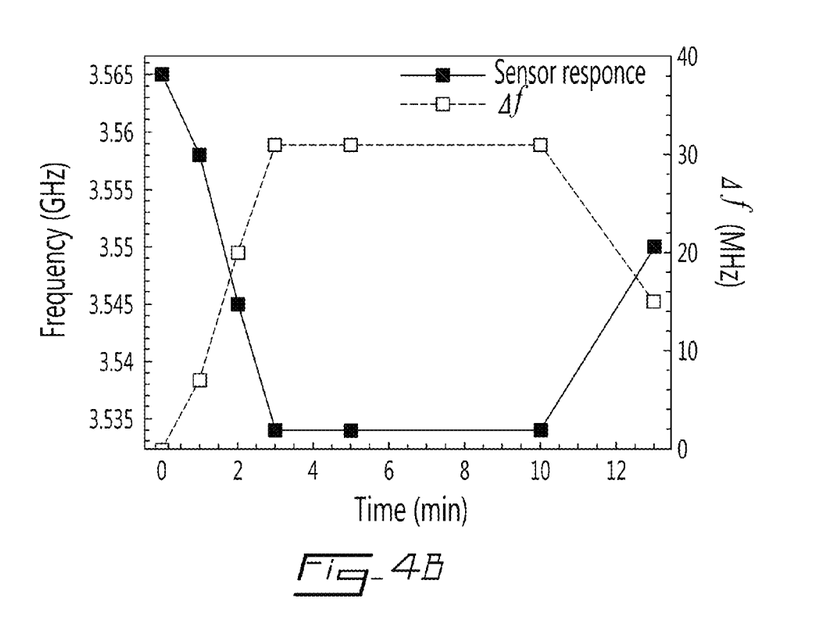
FIG. 4B is a graph showing an example of a resonance frequency of a substrate-integrated waveguide sensor as a function of time when hydrogen is provided then removed in a chamber enclosing the substrate-integrated waveguide sensor.

FIG. 4B is a graph showing the results of an experiment using a SIW sensor functionalized with a tin dioxide nano powder grinded for 60 minutes. The experiment consisted of placing the functionalized SIW sensor in a chamber in which a constant gas flow of hydrogen was provided while measuring the resonant frequency of the SIW sensor. Hydrogen was provided in the chamber at time zero, while it was removed around the tenth minute. It can be seen that a shift in the resonant frequency of the SIW sensor can be observed, indeed, a shift of 40 MHz was measured on the resonance of first order (first mode of resonance). All the measurements were made using a vector network analyser (VNA). It was previously demonstrated that the frequency shift can be due to the change in the dielectric constant of the tin dioxide sensing portions of the SIW sensor. Since the resonance frequency of the microwave resonator is related to the dielectric constant of the microwave resonator by the relation $f_r \propto \in_{eff}^{-1/2}$, where $\in_{eff}$ is the effective permittivity of the substrate, the variation of $\in_{eff}$ can introduce a change in the resonance frequency of the microwave resonator, as discussed above, which can be attributed to a presence of hydrogen.

In another embodiment of the sensor, air can be used as the sensitive dielectric material filing sensing portions of a sensor in order to measure a humidity level in an environment. In this embodiment, the dielectric variation enabling a shift of resonance frequency can be due to the difference between the dielectric constant of air and the dielectric constant of moist air. Therefore, sensing portions having air therein can be used in order to sense the humidity level of the environment. It has been shown that the electric permittivity of air changes as a function of the relative humidity according to the equation:

$$\varepsilon_r(H) = 1 + \frac{211}{T}\left(P + \frac{48P_s}{T}RH\right) \times 10^{-6}; \quad (3)$$

where $\in_r$ is the relative permittivity, T is the absolute temperature (in K), P is the pressure of moist air (in mmHg), Ps is the pressure of saturated water vapor (in mmHg), RH is the relative humidity (in %). Equation (3) shows that the dielectric constant of moist air is proportional to the relative humidity RH. Since the resonance frequency of the microwave resonator is inversely proportional to the effective dielectric constant such as $f_r \propto \in_{eff}^{-1/2}$, changing the relative humidity RH due to vapor, for instance, can consequently change the resonant frequency of the microwave resonator. Henceforth, a shift of resonance frequency can be exploited as an indication of the presence of moisture in the air surrounding the microwave resonator of the SIW sensor.

Figure 5A:
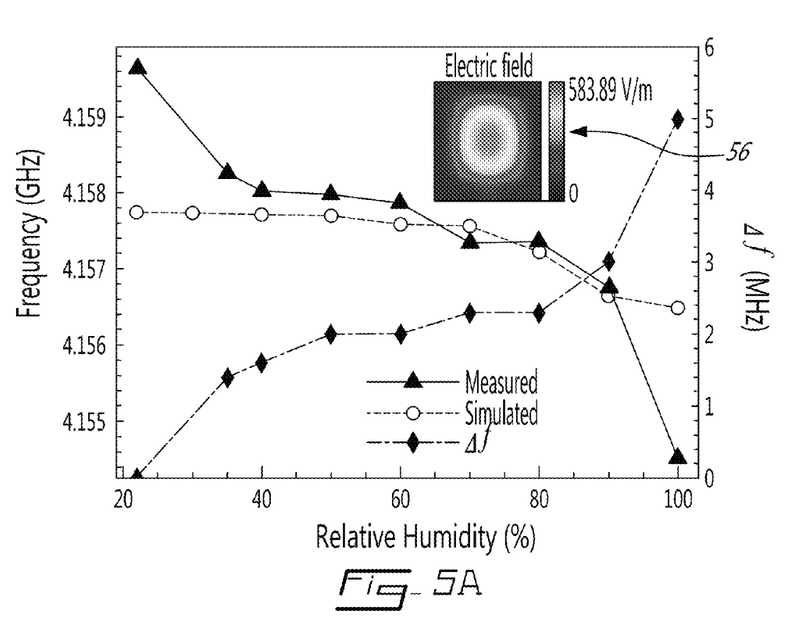
FIGS. 5A and 5B show an example of a simulated and measured resonance frequency of a substrate integrated sensor as a function of relative humidity percentage in an environment of the sensor for the first order of resonance in FIG. 5A and for the second order of resonance in FIG. 5B.
Figure 5B:
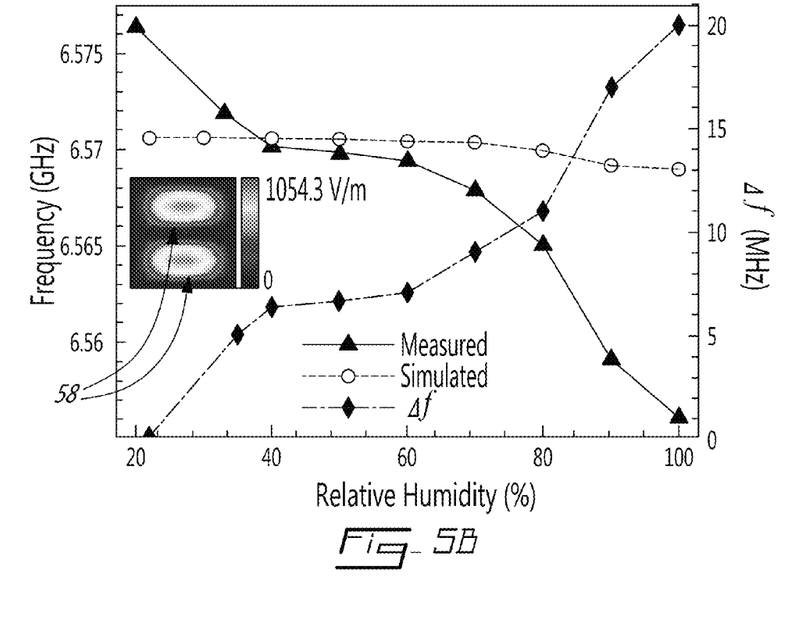

FIGS. 5A-B shows graphs presenting the simulated and measured resonance frequencies as a function of relative humidity RH. In this experiment, the relative humidity RH was increased from 20% to 100%, and the resonance frequencies were measured using a vector network analyser. As shown in FIG. 5A, the first mode of resonance 56 of the microwave resonator, i.e. around 4.16 GHz, exhibits a maximum shift of resonance frequency of 5 MHz from a relative humidity of 20% to a relative humidity of 100%. The measured sensitivity S=|Δf/ΔRH| was found to be 65 kHz/RH, where Δf is the shift of resonance frequency measured, and ΔRH is the range of relative humidity on which the shift Δf was measured. The same measurement was performed on the second mode of resonance 58, i.e. around 6.58 GHz, and the results are shown in FIG. 5B. The resonance frequency of the second order of resonance exhibits a maximum shift of resonance frequency of 20 MHz at a relative humidity of 100%, and a sensitivity of 261 kHz/RH is obtained. It is noticed that the sensitivity of the second mode of resonance is higher than the sensitivity of the first order of resonance, perhaps due to the larger area of the electric field interacting with the sensing portions of the resonator in the case of the second mode of resonance. Accordingly, one can position the sensing portions of the resonance cavities at high intensity areas 56 and 58, thus increasing the interaction between the electric field (as shown in insets of FIGS. 5A and 5B) of the resonance modes and the dielectric material within those strategically positioned sensing portions.

wherein the at least one sensing portion of each of the at least one resonance cavity are located on at least a given high intensity area, the at least a given high intensity area being indicative of a high electric field therearound.

Figure 6A:
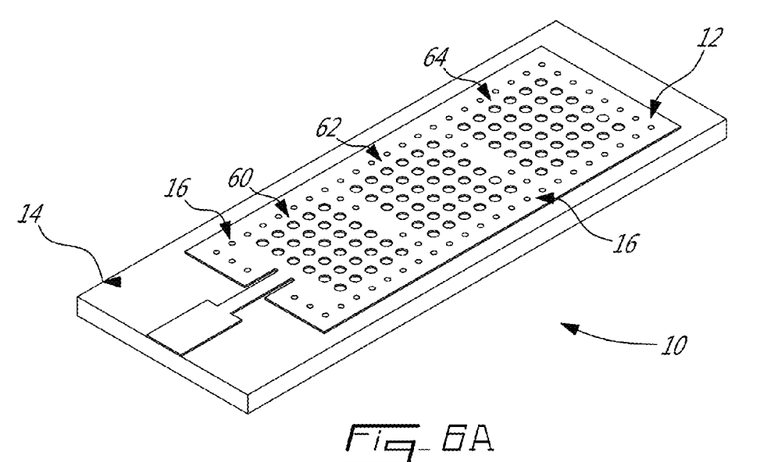
Figure 6B:
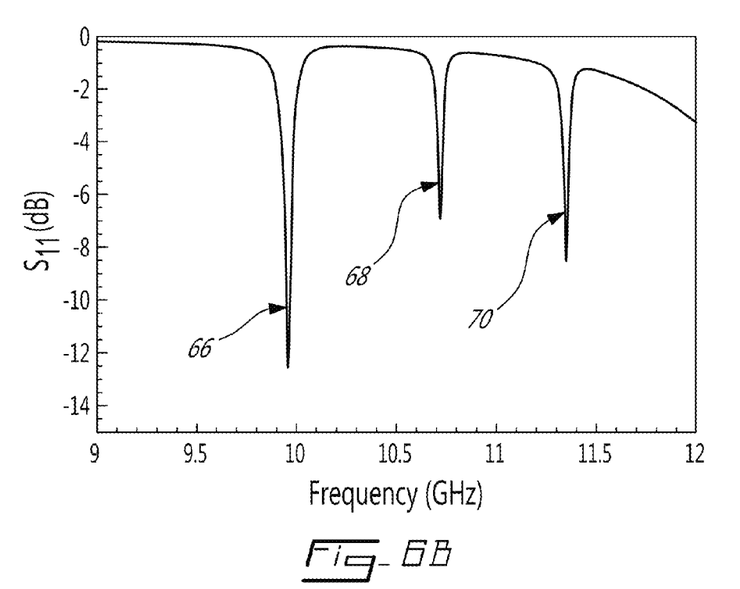
FIG. 6B is a graph showing an example of the resonance frequencies associated with the three resonance cavities of the sensor of FIG. 6A.

In another embodiment, the substrate-integrated waveguide sensor can have more than one resonance cavity on the top conductive surface. As shown in FIG. 6A, the SIW sensor can have three resonance cavities, for instance, each having sensing portions being functionalized with a different sensitive dielectric material. Accordingly, one sensor can be used to sense three different properties of an environment by monitoring the associated signature resonance frequencies corresponding to each of the resonance cavities. For instance, the resonance cavities 60, 62 and 64 can have the resonance frequencies (simulated) 66, 68 and 70. Such an embodiment can be used as a multi gas sensor made out of a monolithic fabrication process. It has to be noticed that to enhance the resonant phenomenon, each resonance cavity can be enclosed partially by the electrically conducting fence, as shown in FIG. 6A. It is understood that although three resonance cavities are shown in FIG. 6A, a substrate-integrated sensor can comprise two resonance cavities or more than three resonance cavities.

Figure 7A:
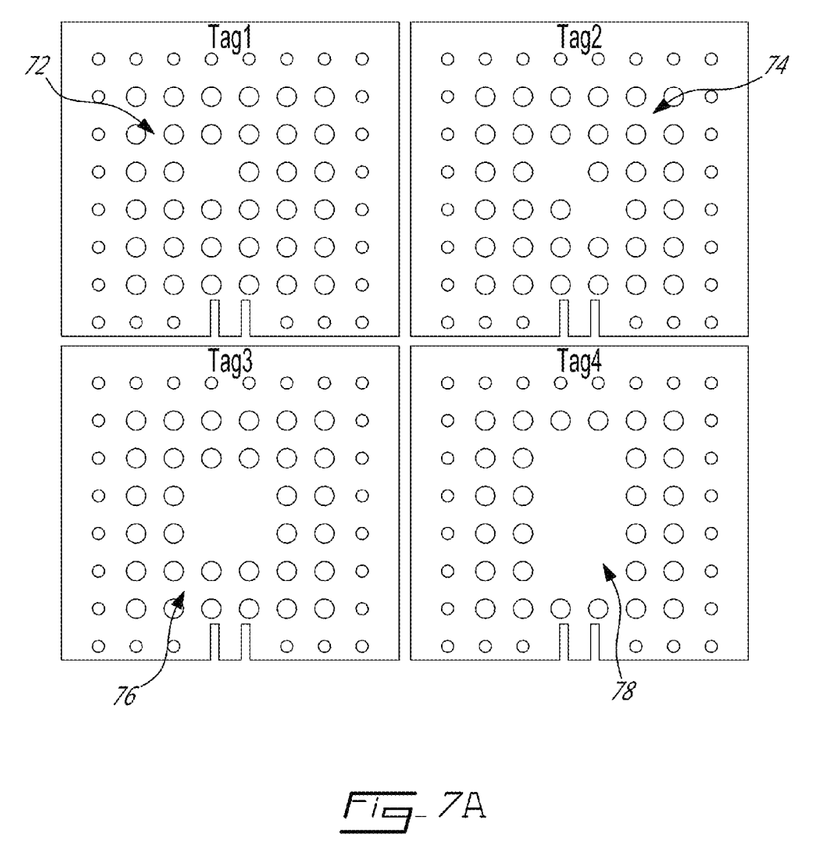
FIG. 7A is a top view of alternate examples of substrate-integrated waveguide sensors, each sensor having a signature pattern of sensing portions.
Figure 7B:
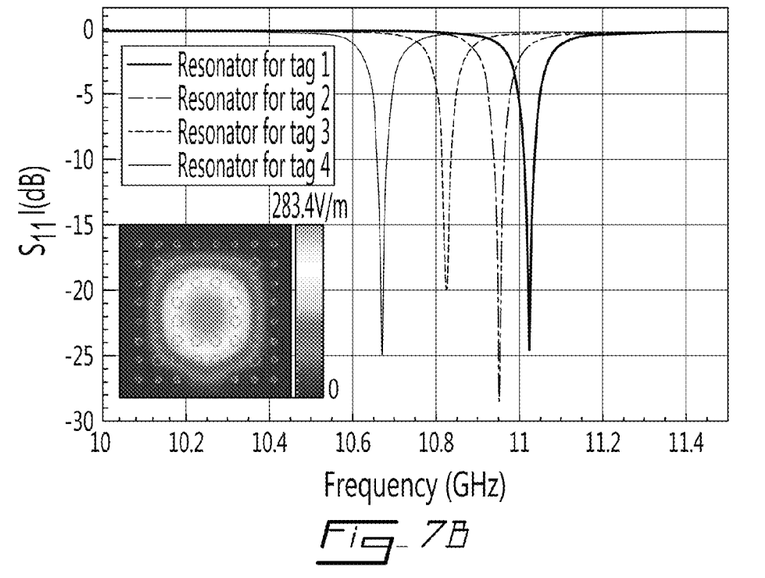
FIG. 7B shows a graph of an example of the simulated resonance frequencies associated with the signature patterns shown in FIG. 7A.
Figure 7C:
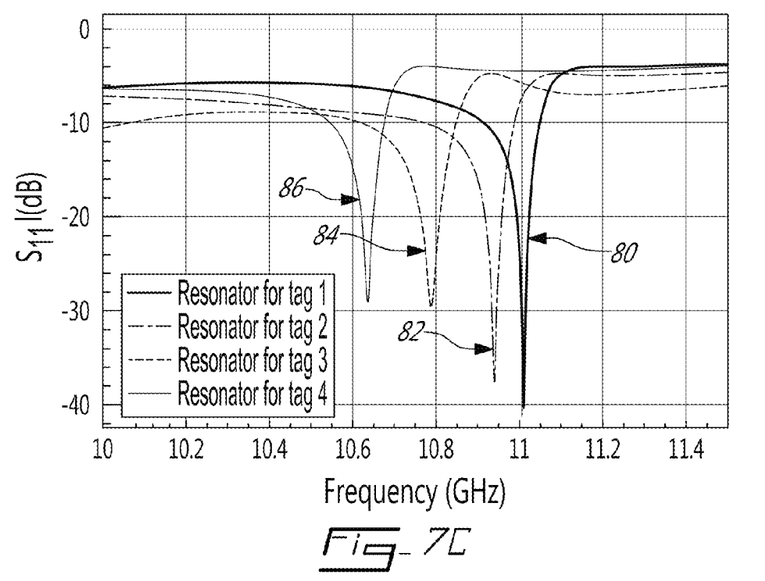
FIG. 7C shows the measured resonance frequencies associated with the signature patterns shown in FIG. 7A.

In another embodiment, the substrate-integrated waveguide sensor 10 can have a given pattern of sensing portions on the top reflective surface of the microwave resonator. Since the resonance frequency is dependent on an effective dielectric constant of the SIW sensor 10 and on a geometry of the microwave resonator, a first SIW sensor having a first given pattern 72 of sensing portions can have a different signature resonance frequency than a second SIW sensor having a second given pattern 74 of sensing portions. Therefore, the four different patterns (72, 74, 76 and 78) of sensing portions shown in FIG. 7A can have four distinct signature resonance frequencies (80, 82, 84 and 86), which can enable to distinguish a SIW sensor from another SIW sensor only by a value of its resonance frequency. For instance, as shown in FIGS. 7B and 7C, the four different patterns of sensing portions presented in FIG. 7A each has a distinct simulated and measured value for their signature resonance frequency.

Figure 8:
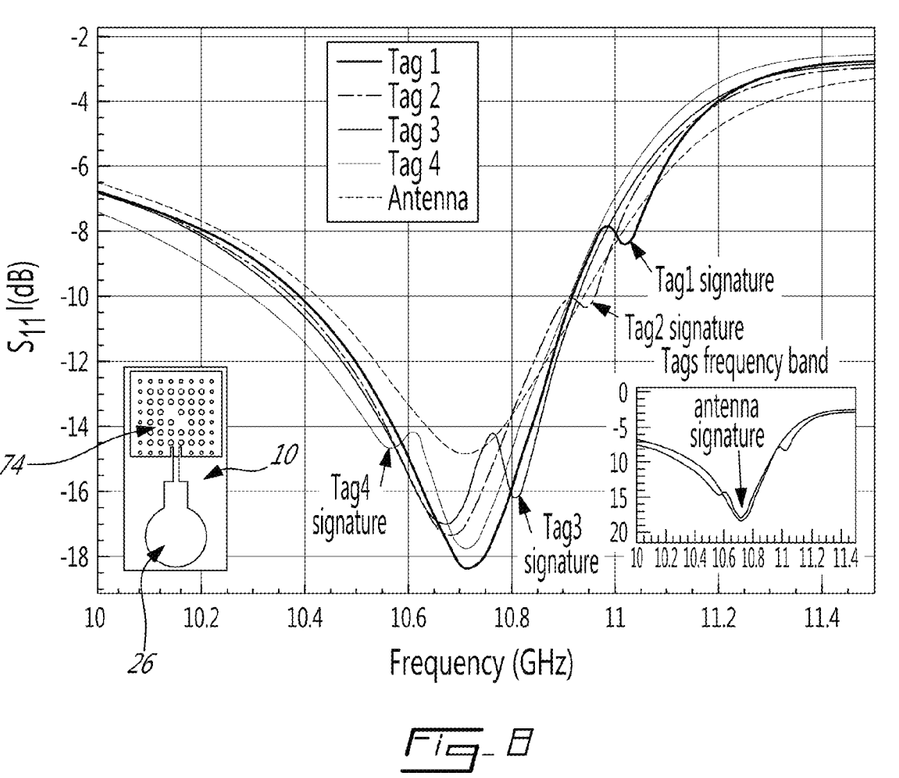
FIG. 8 shows a graph of an example of the measured resonant frequencies associated with the signature patterns of the sensors shown in the graph which has a remote interrogation system involving an antenna.

In another embodiment, the substrate-integrated waveguide sensor 10 can be used in a wireless interrogation system using an antenna 26 as illustrated in the substrate-integrated waveguide sensor shown in FIG. 8. In this embodiment, a broad microwave signal is propagated to the SIW sensor having a given pattern of sensing portions in a resonance cavity of the microwave resonator. Each sensor reflects a portion of the broad microwave signal to form a reflected microwave signal. Accordingly, a VNA can be used to monitor the reflected signal in order to sense a shift of a resonance frequency dip in the reflected signal. The graph shown in FIG. 8 shows an example of a microwave signal of an antenna (black dotted line) along with the microwave signals reflected by SIW sensor having the pattern of sensing portions of the SIW sensor illustrated in FIG. 7A. For each of these four SIW sensors, a different signature resonant frequency can be observed directly on the reflected microwave signal. Indeed, the four curves shown in FIG. 8 each has a particular resonance frequency that can be associated to the corresponding pattern of sensing portions 74. In other words, substrate-integrated waveguide sensors can be remotely interrogated and remotely identifiable based only on their resonance frequencies. Therefore, if a particular SIW sensor is known to have sensing portions being filled with a nano powder of tin dioxide and that its signature resonance frequency is 10.6 GHz and another SIW sensor is known to have sensing portions being filled with air and that its signature resonance frequency is 10.9 GHz. One can send a broad microwave signal towards the two SIW sensors and measure the reflected microwave spectrum. Doing so, one can establish a shift in the resonance frequency around 10.6 GHz and another shift in the resonance frequency around 10.9 GHz in order to determine a change in one or another of the physical properties. For instance, in this situation, the resonance at 10.6 GHz can be associated to the presence of hydrogen while the resonance at 10.9 GHz can be associated with a relative humidity level. Moreover, a substrate-integrated waveguide sensor having a plurality of resonance cavities being filled each with a different dielectric material could have a different pattern (or address) of sensing portions for each of the resonance cavity. In this embodiment, a simple measurement of a reflected microwave signal can indicate a change in the physical property associated to each of the resonance cavities. Furthermore, due to the fact that the sensor structure is functioning in the microwave frequency band, this invention facilitate the possibility of wireless operation addressing applications in harsh environments.

Figure 9:
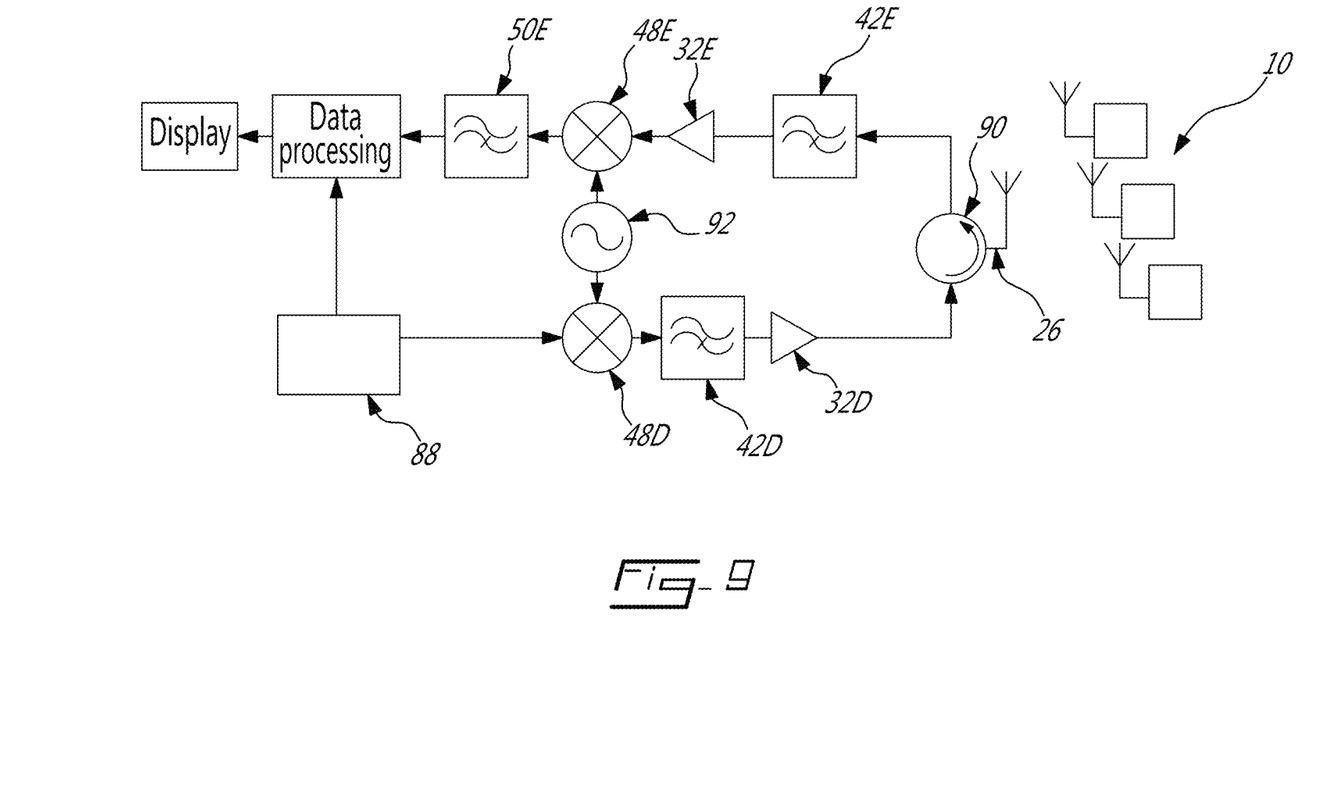
FIG. 9 is a block diagram showing an example of a detection system for remote interrogation of three substrate-integrated waveguide sensors.

FIG. 9 shows a block diagram of an example of a detection system for substrate-integrated waveguide sensors 10 having antennas mounted thereto. In this embodiment, a broad microwave generator 88 can generate a first portion of a reference microwave signal to be propagated to a data processing computer. In a parallel manner, the broad microwave generator 88 can propagate a second portion of the reference microwave signal to a microwave mixer 48D mixing the second portion of the reference microwave signal to a local oscillator signal generated by a local oscillator 92. The mixed signal is subsequently filtered with a high pass filter 42D that is amplified using a microwave amplifier 32D. This amplified signal is passed through a microwave circulator 90 having a port connected to an antenna 26 in order to communicate the signal to the substrate-integrated waveguide sensors 10. The SIW sensor 10 reflects to the antenna 26 an output microwave signal, which is propagated to a second high pass filter 42E, then to a second microwave amplifier 32E, to be subsequently mixed with the local oscillator signal by a second mixer 48E. The resulting signal can be filtered using a low pass filter 50E to form a microwave sensing signal. The data processing computer receives the first portion of the reference microwave signal and the microwave sensing signal in order to compare the two signals to monitor a shift of resonance frequency. Therefore, sensing a physical property of the environment. It is readily understood that other detections schemes incorporating the substrate-integrated waveguide sensors can be used.

The microwave sensor presented herein can be made using straight-forward manufacturing processes and known techniques such as PCB. Henceforth, one can make such a sensor by first placing a substrate layer made of a first dielectric material. Then, one can incorporate a layer of conductive material on the top of the substrate and a layer of conductive material on the bottom of the substrate and then process at least one sensing portion through the three layers thus forming a fence of through-holes enclosing at least one resonance cavity of the three layers, an input channel on the layer of conductive material on the top of the substrate, the input channel protruding to one of the at least one resonance cavity of the three layers, and, on the at least one resonance cavity, a given configuration of holes through at least the layer of conductive material on the top of the substrate and the substrate layer. Subsequently, one can apply a melted layer of conductive material on an interior surface of the through-holes thereby making an electrical link between the two layers of conductive material and finally insert a dielectric material inside the holes of at least an associated resonance cavity. With such straight-forward steps, cheap sensors for sensing physical properties of an environment can be made.

As can be seen therefore, the examples described above and illustrated are intended to be exemplary only. It is readily understood that the sensor can be used in industrial applications, in residential applications, in air quality monitoring applications, in vehicular applications, in energy applications, and in emerging applications. Moreover, it is understood that a width and a length of a resonance cavity having no sensing portions can be sufficient to provide a signature resonance frequency of a SIW sensor. The number of resonance cavities having no sensing portions can be one, or more, depending on the allocated bandwidth of the SIW. Also, the number of resonance cavities to be used can influence the resonance frequency and its bandwidth. Furthermore, it is understood that the fence of via holes enclosing the resonance cavities can be replaced by a fence of conductive material thereby reflecting the microwave input signal within the microwave resonator. In an alternate embodiment, the two conductive layers can be separated from one another by an environmental fluid spacing acting as the first dielectric material, and be interconnected and fixed to one another by the structure of the fence and/or the structure of 'posts' made of a second dielectric material and interconnecting the two conductive layers to one another. In other words, the structure can be provided by the second dielectric material and/or the fence instead of being provided by the first dielectric material, for instance. In addition, it is also understood that the sensor described herein can also be used with signal having radio frequencies (RF). The scope is indicated by the appended claims.

What is claimed is:

1. A sensor for sensing at least a physical property of an environment, the sensor comprising a microwave resonator having a top conductive layer, a bottom conductive layer and a substrate layer made of a first dielectric material sandwiched therebetween, a fence electrically connecting the top conductive layer to the bottom conductive layer across the substrate layer and enclosing at least one resonance cavity, at least one microwave signal port across the fence, at least one sensing portion having a second dielectric material functionalized to the physical property of the environment, the second dielectric material extending across the conductive layers and the at least one resonance cavity and being exposed to the environment during use of the sensor, the microwave resonator having at least one resonance frequency being dependent of the exposure to affect a microwave signal resonating therein.

2. The sensor of claim 1, wherein the at least one sensing portion includes an array of sensing portions, each provided in the form of a hole filled by the second dielectric material.

3. The sensor of claim 1, wherein the fence comprises a plurality of via holes electrically connecting the top conductive layer to the bottom conductive layer.

4. The sensor of claim 1, wherein the dielectric material associated to each of the at least one resonance cavity is sensitive to a physical property to sense.

5. The sensor of claim 2, wherein the resonance frequency associated to each of the at least one resonance cavity is dependent on a signature pattern in which the array of sensing portions is disposed.

6. The sensor of claim 1, wherein the fence partially encloses each of the at least one resonance cavity individually thereby forming resonance subcavities being connected in series along the microwave resonator.

7. The sensor of claim 1, wherein the at least one microwave signal port is used as a microwave output port.

8. The sensor of claim 1, wherein the at least one microwave signal port is electrically connected to at least one of the top conductive layer and the bottom conductive layer.

9. The sensor of claim 1, wherein the at least one microwave signal port is connected to an antenna for receiving the signal in a wireless communication link.

10. The sensor of claim 9, wherein the antenna is made integral to the top conductive layer of the microwave resonator.

11. The sensor of claim 1, wherein the physical property of the environment is a presence of a gas, a relative humidity, a temperature or a dust level.

12. The sensor of claim 1, wherein the conductive layers are made of a metallic material such as copper.

13. The sensor of claim 1, wherein the second dielectric material for sensing presence of hydrogen is tin dioxide.

14. The sensor of claim 1, wherein the second dielectric material for sensing humidity is air.

15. The sensor of claim 1, where the microwave resonator has a rectangular body.

16. The sensor of claim 15, wherein the at least one microwave signal port of the microwave resonator is located in the middle of an edge of the rectangular body.

17. The sensor of claim 1 further comprising a microwave output port for at least transmitting the signal.

18. The sensor of claim 1, wherein the at least a sensing portion of each of the at least one resonance cavity are located on at least a given high intensity area, the at least a given high intensity area being indicative of a high electric field therearound.

19. A method for sensing at least a physical property of an environment, the method comprising:
providing a path having an input and an output; and a microwave resonator therebetween, the microwave resonator having a top conductive layer, a bottom conductive layer and a substrate layer therebetween, the top conductive layer being electrically connected to the bottom conductive layer by a conductive fence across the substrate layer, the fence enclosing at least one resonance cavity, the input being connected to the at least one resonance cavity across the fence, each of the at least one resonance cavity having at least one sensing portion of a second dielectric material functionalized to the physical property of the environment, extending in the at least one resonance cavity and being exposed to the environment across at least one of the top conductive layer and the bottom conductive layer, the microwave resonator having at least one resonance frequency;
propagating an input microwave signal into the input of the path, the microwave resonator transforming the input microwave signal into an output microwave signal being characterized by the at least one resonance frequency, the at least one resonance frequency being dependent of the exposure of the second dielectric material with the environment to affect a microwave signal resonating therein;
measuring the resonance frequency in the output microwave signal from the output of the path; and
sensing the at least a physical property based on the resonance frequency.

20. The method of claim 19, wherein said providing further comprises providing a two-dimensional pattern of sensing portions in at least one resonance cavity of the microwave resonator, each of the two-dimensional pattern of sensing portions imparting a signature resonance frequency to the microwave resonator.

21. The method of claim 20 further comprising associating the signature resonance frequency to a corresponding resonance cavity.

22. The method of claim 20, wherein the resonance frequency of each of the at least one resonance cavity is recognizable based on the two-dimensional pattern of sensing portions.

23. The method of claim 19, wherein said propagating further comprises receiving the input microwave signal via an antenna connected to the input.

24. The method of claim 23, wherein said propagating further comprises transmitting the output microwave signal using an antenna connected to the output.

25. A method of making a sensor for sensing at least a physical property of an environment, the method comprising:
   providing a substrate layer made of a first dielectric material;
   incorporating a layer of conductive material on the top of the substrate and a layer of conductive material on the bottom of the substrate;
   forming a fence of through-holes surrounding a sensing portion except for an input area;
   filling the through-holes with a conductive material thereby making an electrical link between the two layers of conductive material and enclosing at least one resonance cavity; and
   processing a given configuration of holes across the resonance cavity, the holes being interspaced from one another in the sensing portion.

26. The method of claim 25 further comprising inserting a dielectric material inside the holes of at least an associated resonance cavity.

* * * * *